(12) United States Patent
van der Steen et al.

(10) Patent No.: US 8,308,643 B2
(45) Date of Patent: Nov. 13, 2012

(54) THREE-DIMENSIONAL TISSUE HARDNESS IMAGING

(75) Inventors: Antonius Franciscus Wilhelmus van der Steen, Rotterdam (NL); Christoffel Leendert de Korte, Driebergen (NL); Frits Mastik, Rotterdam (NL); Johannes Antonius Schaar, Rotterdam (NL)

(73) Assignee: Stichting voor de Technische Wetenschappen, Utrecht (NL)

( * ) Notice: Subject to any disclaimer, the term of this patent is extended or adjusted under 35 U.S.C. 154(b) by 1835 days.

(21) Appl. No.: 10/790,618

(22) Filed: Mar. 1, 2004

(65) Prior Publication Data

US 2005/0033199 A1    Feb. 10, 2005

Related U.S. Application Data

(63) Continuation of application No. PCT/NL02/00572, filed on Sep. 2, 2002.

(30) Foreign Application Priority Data

Aug. 31, 2001    (NL) .................................... 1018864

(51) Int. Cl.
   *A61B 8/14*    (2006.01)
   *A61B 8/00*    (2006.01)
   *A61B 8/12*    (2006.01)

(52) U.S. Cl. ....................................................... 600/438

(58) Field of Classification Search .................. 600/462, 600/587, 443, 561, 407, 103, 438–440, 463; 73/787, 818
See application file for complete search history.

(56) References Cited

U.S. PATENT DOCUMENTS

| 5,125,410 | A |   | 6/1992 | Misono et al. |
| 5,195,521 | A |   | 3/1993 | Melton, Jr. et al. |
| 5,307,816 | A |   | 5/1994 | Hashimoto et al. |
| 5,524,636 | A | * | 6/1996 | Sarvazyan et al. ............ 600/587 |
| 5,622,174 | A |   | 4/1997 | Yamazaki |
| 5,785,663 | A | * | 7/1998 | Sarvazyan .................... 600/587 |
| 5,800,356 | A |   | 9/1998 | Criton et al. |
| 5,848,969 | A | * | 12/1998 | Panescu et al. ............... 600/462 |
| 6,099,471 | A | * | 8/2000 | Torp et al. .................... 600/438 |

(Continued)

FOREIGN PATENT DOCUMENTS

EP    0 908 137 A1    4/1999

(Continued)

OTHER PUBLICATIONS

Johnson et al, The Probability Density of Spectral Estimates Based on Modified Periodogram Averages, IEEE Transactions on Signal Processing, vol. 47, No. 5, May 1999, p. 1255-1261.*

(Continued)

*Primary Examiner* — Brian Szmal
(74) *Attorney, Agent, or Firm* — Leydig, Voit & Mayer, Ltd.

(57) ABSTRACT

A method for generating hardness information of tissue subject to a varying pressure. The method comprises receiving signals from the tissue from a sensor for measuring the deformation of the tissue in a measuring plane defined by the sensor, which sensor, during a varying pressure exerted on the tissue, is moved along the tissue in a direction transverse to the measuring plane; identifying strain of the tissue from the resulting signals; and relating the strain to elasticity and/or hardness parameters of the tissue. The method may comprise the step of displaying elasticity and/or hardness parameters of a tissue surface or tissue volume part extending practically parallel to the direction of motion of the sensor.

25 Claims, 4 Drawing Sheets

1. Apparatus    9. Plaque
2. Catheter    10. Fat core
3. Sensor    11. Harder cap
4. Processor    12. Actuator
5. Display device    13. Activating
6. Position recording    14. ECG device
7. Blood vessel    15. Data storage
8. Vessel wall    16. Correlation detection

U.S. PATENT DOCUMENTS

2003/0220556 A1* 11/2003 Porat et al. .................. 600/407

FOREIGN PATENT DOCUMENTS

| JP | 03-151947 A | 6/1991 |
| JP | 04-017843 A | 1/1992 |
| JP | 05-161653 A | 6/1993 |
| JP | 05-317313 A | 12/1993 |
| JP | 06-078926 A | 3/1994 |
| JP | 07-055775 A | 3/1995 |
| JP | 10-248844 A | 9/1998 |
| JP | 11-151246 | 6/1999 |
| JP | 11-188036 A | 7/1999 |
| JP | 2000-229078 A | 8/2000 |
| JP | 2000-254129 A | 9/2000 |
| JP | 2000-316865 A | 11/2000 |
| JP | 2001-161693 A | 6/2001 |
| JP | 2001-224594 A | 8/2001 |
| JP | 2002-509748 A | 4/2002 |
| WO | WO 94/23652 | 10/1994 |
| WO | WO 99/49782 A1 | 10/1999 |
| WO | WO 01-008561 A1 | 2/2001 |
| WO | WO 03/017845 | 3/2003 |

OTHER PUBLICATIONS

Encyclopedia Britannica article on Arteries, 2009.*
PCT International Preliminary Examination Report, PCT/NL02/00572, dated Jul. 22, 2003.
C. L. de Korte at al., "Intravascular Elasticity Imaging Using Ultrasound: Feasibility Studies in Phantoms," *Ultrasound in Medicine and Biology*, vol. 23, No. 5, May 1997, USA, pp. 735-746.
K. Yamamoto et al., "An intravascular Ultrasonic Imaging Technique for Measurement of Elastic Properties of the Artery," *Acoustical Imaging*, vol. 20, Sep. 23, 1992, pp. 433-440.
K. Ryan et al., "A High Frequency Intravascular Ultrasound Imaging System for Investigation of Vessel Wall Properties, " *IEEE* 1992, Ultrasonics Symposium, vol. 2, Oct. 20-23, 1992, Tucson, AZ, USA, pp. 1101-1105.

* cited by examiner

1. Apparatus
2. Catheter
3. Sensor
4. Processor
5. Display device
6. Position recording
7. Blood vessel
8. Vessel wall
9. Plaque
10. Fat core
11. Harder cap
12. Actuator
13. Activating
14. ECG device
15. Data storage
16. Correlation detection

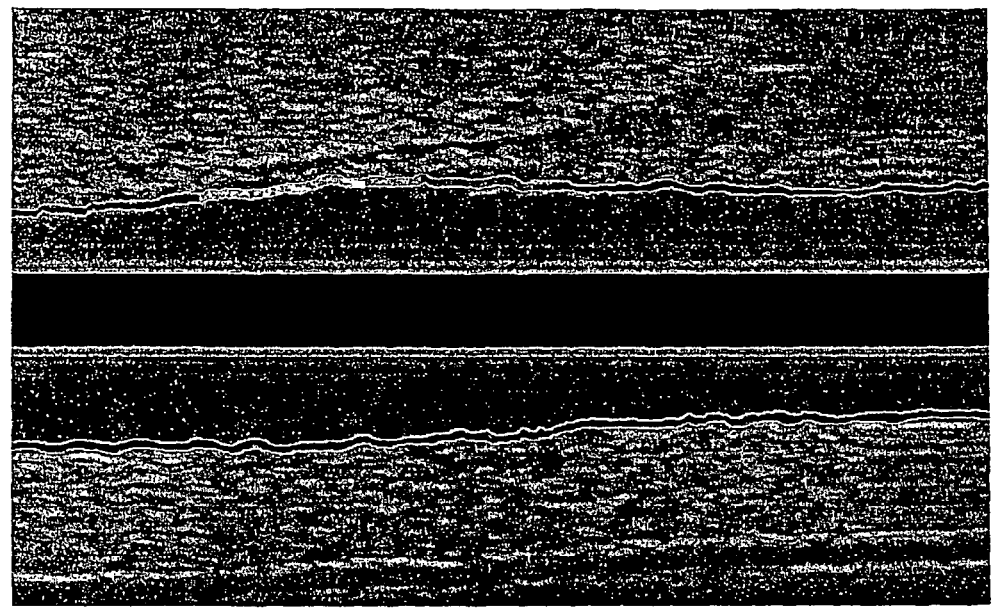
Fig. 2b
Fig. 2a

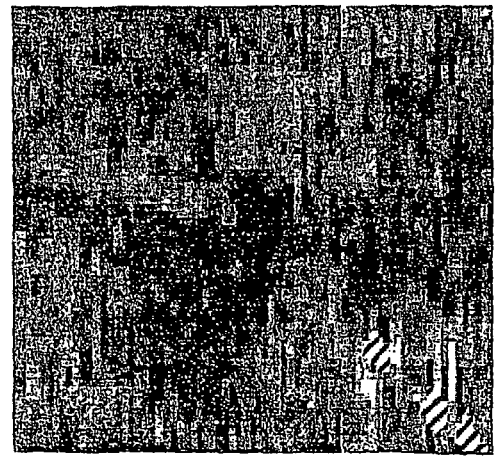 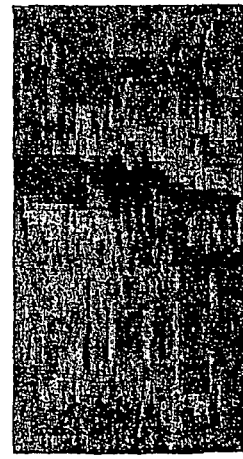 
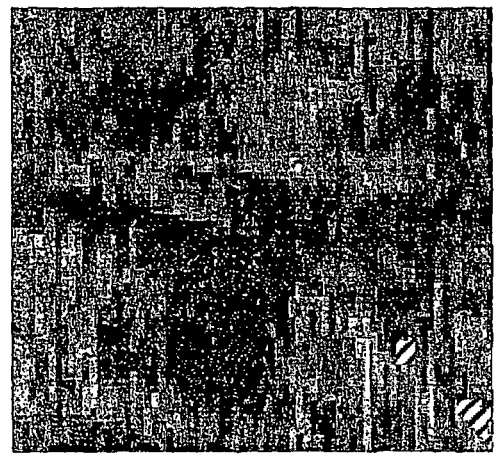  
 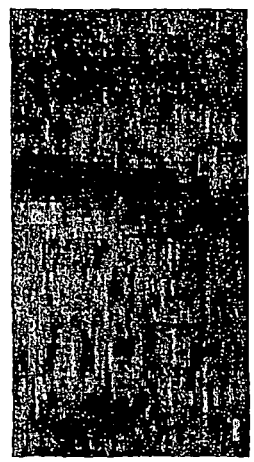 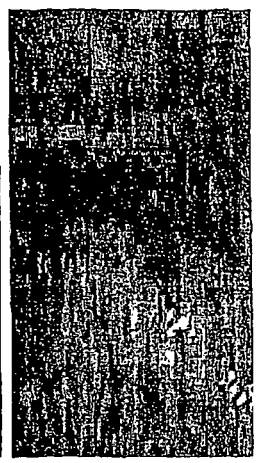
1mm/s  0,5mm/s
Fig. 3a   Fig. 3b   Fig. 3c

THREE-DIMENSIONAL TISSUE HARDNESS IMAGING

CROSS-REFERENCE TO RELATED APPLICATION

This application is a continuation of PCT International Patent Application No. PCT/NL/02/00572, filed on Sep. 2, 2002, designating the United States of America, and published, in English, as PCT International Publication No. WO 03/017845 A1 on Mar. 6, 2003, the contents of the entirety of which is incorporated by this reference.

TECHNICAL FIELD

This invention relates to a method for generating hardness information of tissue subject to a varying pressure. In particular, the method relates to a method for generating hardness information of the wall of a blood vessel or body cavity.

BACKGROUND

Such a method is known from European patent application EP-A 0 908 137. In this application, the strain (deformation) of vessel walls is derived with ultrasound from the relative displacement of a more inward layer and a more outward layer of the vessel wall as a result of the pressure varying through the heartbeat. These relative displacements are (at an assumed equal speed of sound in the medium) equal to the difference of relative time delays of the ultrasound beam, measured at two times.

The relative time delay can be measured by correlating with each other sound signals obtained consecutively over time from one specific direction and deriving the relevant time delay from a correlation optimum. At this optimum, therefore, two signals consecutive over time are maximally correlated when the time difference between the respective signals is equal to the relevant time delay. By taking the difference of time delays measured at two different times and relating this to the time difference between the measuring times, it is possible to derive the degree of strain of the vessel wall in the direction of the sound beam as a result of pressure changes induced by the heartbeat.

By measuring the local relative displacements with a measuring beam in a specific direction and performing this measurement in a measuring plane oriented transversely to the vessel wall, it is possible to display elasticity information about respective measuring positions in the measuring plane. Furthermore, by measuring an average relative displacement along the above directions, a so-called palpogram can be composed, which is indicative of the hardness of the vessel wall in the plane in which the vessel wall cuts the measuring plane. The information derivable from such an elastogram/palpogram is important to identify and characterize plaques on the vessel walls. The composition of plaques can be important to the assessment of their injuriousness to health.

Such information is often not derivable from a conventional echogram, since the image of high-risk cannot be distinguished from less high-risk plaques.

Moreover, practical and theoretical studies show that the degree of strain of the vessel wall is indicative of the stresses that can occur in such plaques. If the stresses become too high, a plaque can tear open, so that a life-threatening thrombosis can arise.

Although for a two-dimensional cross-section, satisfactory measuring results can be obtained, in practice there appears to be a need for a three-dimensional display of the hardness information of the wall, so that the elasticity/hardness of at least one surface part of the vessel wall can be measured. With the present technique, it is practically very difficult to reproducibly analyze a blood vessel in such a manner. Furthermore, on the basis of conventional echographic data it is very hard to localize a suspect spot in a blood vessel. In fact, the performance of a single transverse scan at selected positions in a blood vessel provides insufficient information to enable determination of the presence or absence of plaques in the blood vessel as a whole.

DISCLOSURE OF THE INVENTION

The invention meets such needs and provides a method with which 3D information about the elasticity and/or hardness of a wall of a body cavity, in particular a blood vessel, can be obtained in a consistent and reproducible manner. In this regard, it is observed that with the present conventional technique the correlation between consecutive images is optimized by positioning the sensor as stably as possible, because movement of the sensor in general has a negative effect on the correlation. The invention is based on the insight that precisely by performing a motion transverse to the measuring plane a sufficient correlation between consecutive images can be maintained to enable detection of hardness and/or elasticity properties.

Accordingly, the method comprises the following steps of:
  receiving signals from the tissue with a sensor for measuring the deformation of the tissue in a measuring plane defined by the sensor, which sensor, during a varying pressure exerted on the tissue, is moved along the tissue in a direction transverse to the measuring plane;
  identifying strain of the tissue from the resulting signals; and
  relating the strain to elasticity and/or hardness parameters of the tissue.

According to the invention, signals are received from, e.g., a vessel wall in a preferably almost continuous motion, consecutive (groups of) frames still having a sufficient correlation to enable distillation of the relevant information. This can be determined by means of a probability function indicating the relation between consecutive images. By controlling the motion (or feeding back feedback position) related to this probability function, an optimum palpogram quality is obtained, which can even be more favorable than in a stationary arrangement.

The method preferably comprises the step of displaying elasticity and/or hardness parameters of the tissue surface or tissue volume part extending practically parallel to the direction of motion of the sensor, if required, combined with position information of the sensor and/or the tissue. The deformation can be determined with an acoustic or optical sensor detecting echographic or optical data.

In a further preferred embodiment, signals possessing an optimum overlap are received. An optimum overlap can be determined by means of a probability function displaying the similarity between consecutive signals.

In the alternative or in addition thereto, at an assumed cyclic pressure change, signals can be received at predetermined time intervals in the period of the motion. In a preferred embodiment, these are signals of a blood vessel wall, the data being received only during a specific time interval of the period of the heartbeat. An advantage thereof is that signals that are not or less suitable for the determination of elasticity and/or hardness information of the tissue need not be stored, as a result of which data storage capacity can be performed to a limited extent, and the data processing can be significantly simplified.

The invention has a special use in case the tissue is an artery moving through the heartbeat in the longitudinal direction. In that case, the sensor can be moved practically parallel to this direction, so that during at least one detection period, the sensor is in a practically fixed position relative to the tissue. Practice shows that in particular in or near the heart, where relatively strong longitudinal motions of the artery occur, a strongly improved recording of hardness and/or elasticity properties, compared to the conventional recording technique, is obtained in a measuring plane transverse to the vessel wall.

The invention further relates to an apparatus for using the method according to the invention, comprising:

a sensor movable through a blood vessel or body cavity for recording signals from the tissue;

a processor device for collecting and processing signals from the sensor to identify strain of the tissue and to relate the strain to elasticity and/or hardness parameters of a tissue surface or tissue volume part extending practically parallel to the direction of motion of the sensor; and a display device for displaying elasticity and/or hardness parameters of the tissue surface or tissue volume part.

In a preferred embodiment, the apparatus further comprises a position recording means coupled with the processor device to record sensor positions. The position recording means can display the 3D coordinates of the sensor relative to a fixed reference, e.g., by means of (electromagnetic) bearings, or in a simpler embodiment it may be a relative linear measure from, e.g., the point where a catheter is inserted or from a specific fixed location in a blood vessel.

In a mechanized use, the apparatus may be provided with an actuator for moving the sensor. Preferably, the actuator has an adjustable speed of motion. Position recording may thereby occur by means of measuring and/or adjusting the speed of motion of the sensor and/or the actuator.

In a further preferred embodiment, activating means are provided to activate data storage means for recording signals. Further activating means may be provided to activate the actuator. The activating means may be connected with an ECG recording device. In this manner, signals can be received from a blood vessel, the data being received only during a specific time interval of the period of the heartbeat. In the alternative or in addition thereto, the activating means may detect the correlation between consecutive echographic images and activate the data storage means at a the predetermined correlation.

In another further preferred embodiment, the sensor is arranged in a catheter, which can be inserted into a blood vessel, which sensor can record signals under controlled pullback of the catheter.

BRIEF DESCRIPTION OF THE DRAWINGS

The invention will further be explained on the basis of the description of the drawings, in which:

FIG. 2a is a 3D palpogram of a phantom with a soft plaque part;

FIG. 2b is a longitudinal section of the 3D palpogram of FIG. 2a, combined with conventional echographic information;

FIG. 3 is a series of six 3D palpograms of a similar aorta part of a rabbit, obtained in six different measurements.

DETAILED DESCRIPTION OF THE INVENTION

Figure 1:
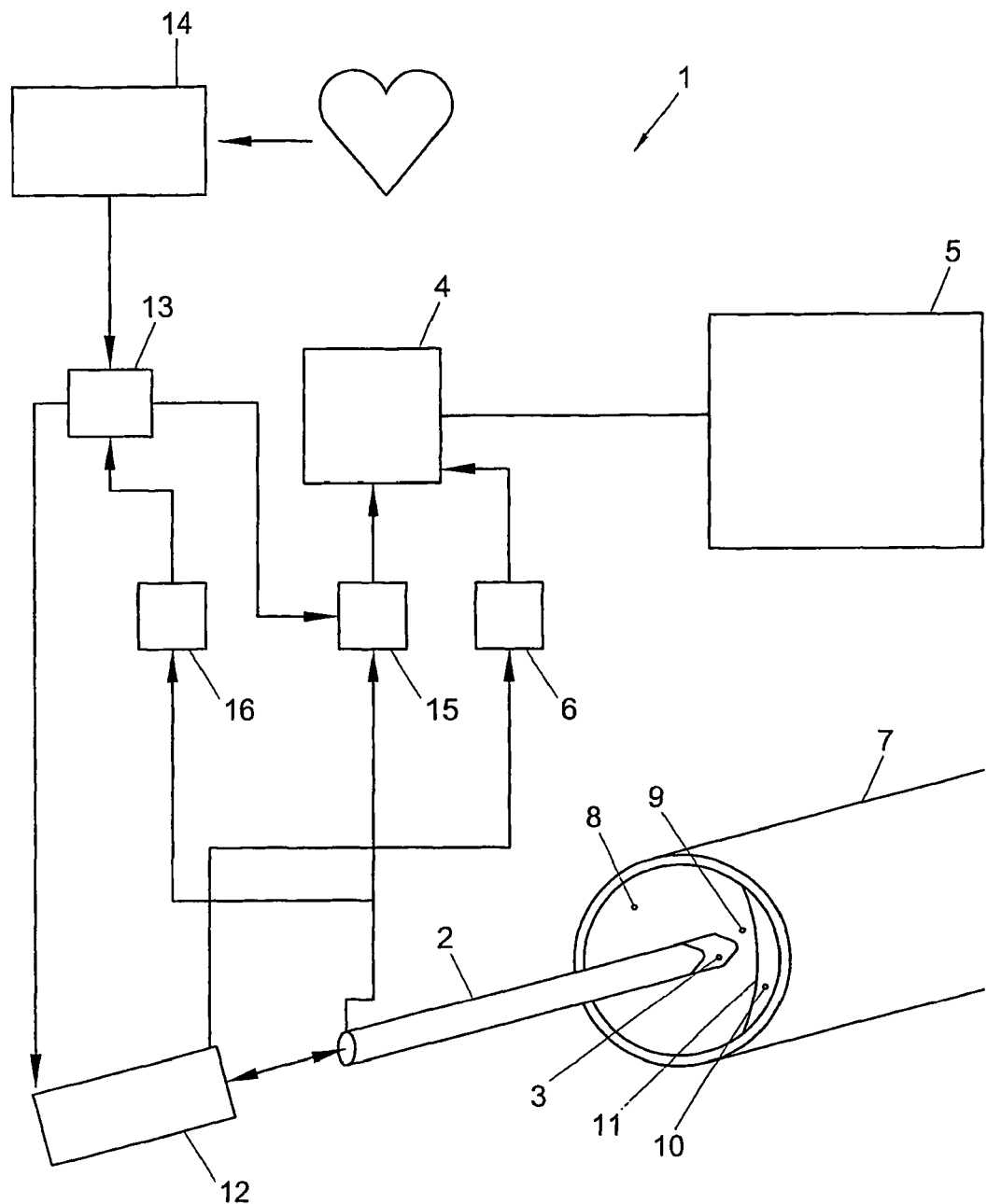
FIG. 1 is a diagrammatic representation of the apparatus according to the invention.

FIG. 1 is a diagrammatic representation of the apparatus 1 according to the invention. This apparatus comprises a movable catheter 2 provided with an acoustic sensor 3. A processor 4 is present to collect and process echographic data; the processor 4 is connected with a display device 5. The processor 4 is further in contact with a position recording means 6 for recording the position of the sensor 3.

The catheter 2 can be moved through a blood vessel 7, which blood vessel 7 has a vessel wall 8 deformed by the heartbeat. The deformation can be derived by the processor 4 from the echographic data of the catheter 2 and related to elasticity and/or hardness parameters of the wall 8.

In explanation, a plaque 9 is shown in the blood vessel 7. This plaque comprises a fat core 10 closed by a harder cap 11. The motion of the catheter 2 is controlled by an actuator 12. The actuator 12 has an adjustable speed of motion, such that the catheter can be moved at a speed of 0.1-2 mm/s. The preferred direction is a so-called pullback direction, i.e. the catheter 2 is inserted until a maximum insertion depth and is then pulled back by the actuator 12. The actuator can pull the catheter 2 back in a practically continuous motion. The actuator 12 can be activated by the activating means 13.

In the alternative, the activating means 13 can be controlled by data from an ECG device 14, so that a favorable moment of the heartbeat can be selected to perform a measurement. This will be explained below in more detail. During the performance of the measurement, the motion can be interrupted, so that an intermittent pullback motion can be performed. The activating means 13 can also be coupled with a data storage means 15 for storing echographic data. This ensures that the extensive amount of echographic data is received only during a relevant part of the heartbeat, which results in a favorable capacity saving and significantly simplifies the data processing.

Besides through selection of a relevant part of the heartbeat for the performance of the palpographic measurement, the activating means can be connected, additionally or alternatively, with correlation-detection means 16 detecting the correlation between consecutive echographic images to become active at a predetermined correlation.

The method according to the invention will be explained below. At a varying pressure as a result of the heartbeat, echographic data are received by the acoustic sensor 3, while the sensor 3 is moved along the vessel wall 8. The echographic data can be analyzed by a processor 4, strain of the vessel wall 8 being identified from the resulting echographic data; and the strain being related to elasticity and/or hardness parameters of the vessel wall 8. In this manner, it is possible to display elasticity and/or hardness parameters of a tissue surface or tissue volume part extending practically parallel to the direction of motion of the sensor. In a preferred embodiment, in such a display, i.e., a palpogram or an elastogram of the vessel wall, the position information of the sensor and/or the tissue is displayed as well. The motion can be a practically continuous motion; in the alternative, an intermittent motion can be performed. The motion and/or the analysis of echographic data can be controlled, so that the echographic data are received at predetermined time intervals in the period of the heartbeat, at which time interval the motion may be interrupted.

In the alternative, only those signals possessing an overlap can be received. An optimum overlap can be determined by means of a probability function displaying the similarity between consecutive signals.

The palpogram of FIG. 2a has been obtained by scanning a phantom with a soft inclusion, shown in cross-section by the echogram of FIG. 2b. The phantom has the shape of a hollow tube and is made of polyvinyl alcohol cryogel. The inclusion comprises a harder cap, which may also be present in a naturally formed plaque. The thickness of the cap varies from 2 mm to 800 µm.

The inclusion thus has mechanical properties corresponding to those of a plaque that may be present in a natural blood vessel.

The phantom was kept under water and subjected to a pulsatile pressure. A catheter provided with an acoustic converter was moved through the phantom at a speed of 1.0 mm/s. The number of acquired frames was about 30 per second, i.e., an axial displacement of 0.03 mm per image. At a beam width of about 0.6 mm, this proved to be an acceptable amount.

In the soft part, a strain until 1% was observed. The strain increases with a decreasing thickness of the cap.

The palpograms of FIG. 3 have been obtained by scanning an artherosclerotic aorta of a New Zealand White rabbit at a pullback speed of 0.5 and 1 mm/s, respectively. In this Figure, a) is a first scan; b) is a second scan obtained after the catheter was positioned again; and c) is a scan obtained some time after, with the catheter again being inserted into the animal.

The palpograms have been obtained at a speed of motion of the catheter of 1.0 mm/s. In the palpograms, the plaque is always clearly visible as a lighter region.

In all cases, the following measuring method was used:
1. contour detection;
2. selection of frames with a minimum mutual motion;
3. estimating the displacement of the wall between two frames;
4. deriving the strain;
5. averaging the strain per angle;
6. (color) coding the strain at the contour.

Figure 4:
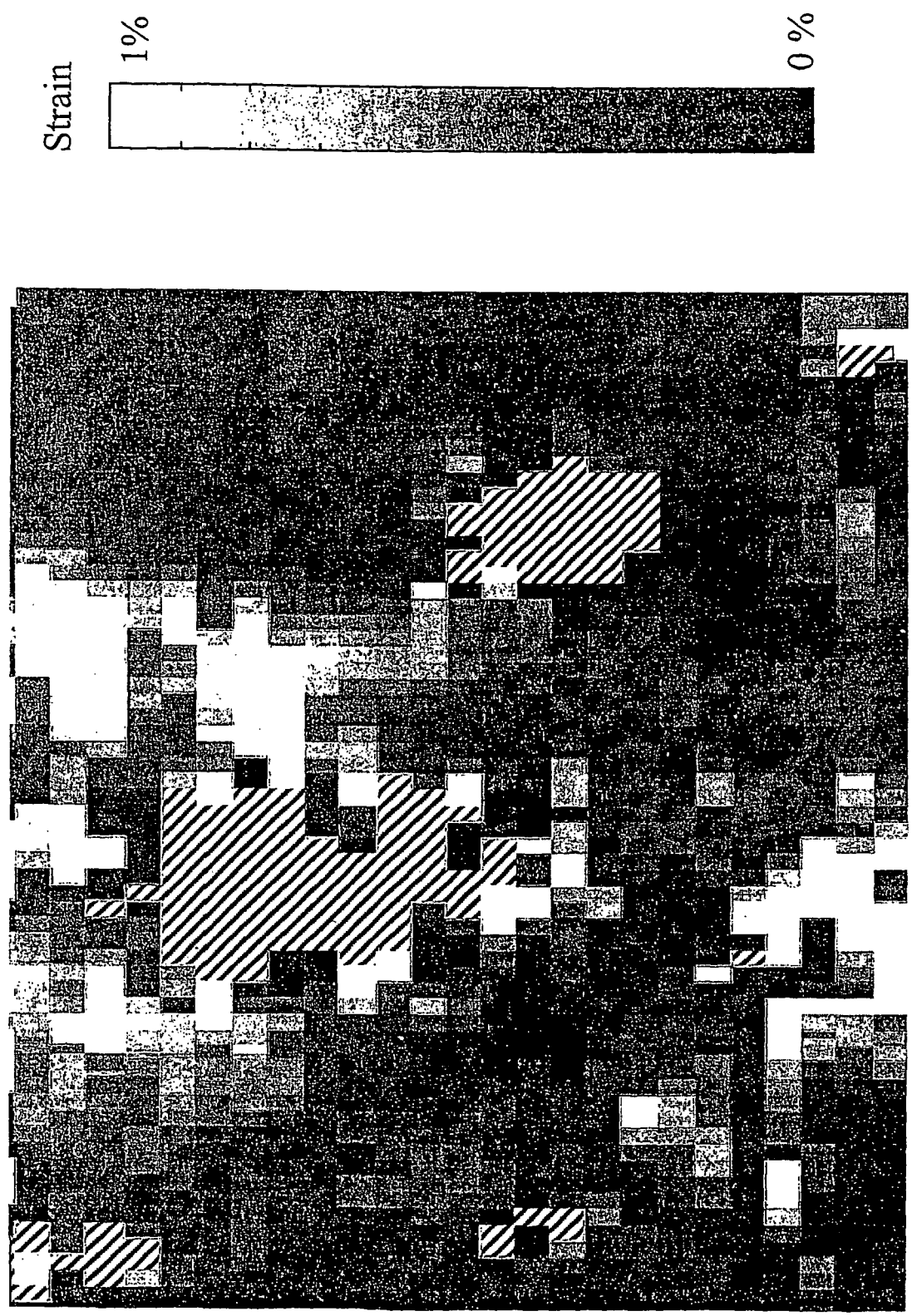
FIG. 4 is a 3D palpogram of a human coronary artery, obtained in vivo.

Of three patients a palpogram was obtained; FIG. 4 shows an example thereof. The hatched regions do not represent available measuring values, as a result of the presence of a side branch of the aorta. As appears from the figure, the largest strain occurs in the regions around the side branch (light regions). It turned out that the motion of the catheter was slight enough to determine a reliable palpogram during a heartbeat. The degree of overlap between consecutive frames always remained at least about 70%.

In an experiment, a palpogram was obtained in which the data were divided into heart cycles, using the R-wave of the ECG signal. Because of the natural motion of the catheter through the varying speed of flow of the blood and the contraction of the heart, the catheter moves deeper into the coronary artery during the diastolic phase. Therefore, measurement is performed during this phase (i.e., a decreasing pressure of the heart and an increasing speed of flow), and the catheter is pulled out against the natural motion. This was done at a speed between 0.5 and 1.0 mm/s, by means of a mechanical actuator (Trakback, JoMed Imaging, Rancho Cordova, Calif., USA).

It turned out that through this motion the sensor, during the detection period, has a practically fixed position relative to the wall of the artery. It was found that the motion from the measuring plane is minimized, so that the quality of the palpogram is improved.

Although the invention has been discussed on the basis of the above-mentioned exemplary embodiment, in which the presence of plaques in a blood vessel was checked, it is clear that the invention can also be used when detecting and analyzing other tissues, such as (for cancer research of) the prostate, the esophagus etc. Instead of measuring deformations as a result of a naturally varying pressure, the apparatus can be provided with means for artificially exerting a pressure variation on the tissue.

Furthermore, all kinds of variations and modifications may be used without departing from the spirit of the invention. Such variations may, e.g., comprise the display of a 3D palpogram as a stack of 2D palpograms; the display of the angle at which measurement is performed; or a combination display of a palpogram and an angiogram.

Such and other variations are deemed to be within reach and the scope of protection of the appended claims.

What is claim is:

1. A computer implemented method for generating hardness information of tissue subject to a varying pressure, the method comprising:
   receiving signals from a tissue with a sensor for measuring the deformation of the tissue in a measuring plane defined by the sensor, where the sensor is moved, under control of an actuator, during the receiving signals step:
   (a) in a direction transverse to the measuring plane, and
   (b) while the tissue is subject to a varying pressure;
   identifying strain of the tissue from the signals received by the sensor moved during the receiving signals step in the direction transverse to the measuring plane; and
   relating the strain to at least one of either hardness or elasticity parameters of the tissue; and
   wherein moving the sensor under control of the actuator, in the direction transverse to the measuring plane while the tissue is subject to a varying pressure, is controlled to provide sufficient correlation between consecutive image frames generated from the signals received by the sensor to identify strain of the tissue.

2. The computer implemented method according to claim 1, wherein the method comprises:
   correlating signals acquired consecutively over time, where the signals are representative of the deformation of the tissue at positions of the sensor moved with respect to other positions of the sensor; and
   calculating, by use of said correlating signals step, strain in a tissue surface or tissue volume part extending parallel to the direction of motion of the sensor.

3. The computer implemented method according to claim 1, wherein the method comprises the step of displaying elasticity and/or hardness parameters of a tissue surface or tissue volume part.

4. The computer implemented method according to claim 1, wherein the signals are echographic data detected with an acoustic sensor.

5. The computer implemented method according to claim 1, wherein the signals are optical data detected with an optical sensor.

6. The computer implemented method according to claim 1, wherein the method comprises displaying elasticity and/or hardness parameters of the tissue with position information of the sensor and/or the tissue.

7. The computer implemented method according to claim 1, wherein the signals are received during continuous motion of the sensor.

8. The computer implemented method according to claim 1, wherein signals possessing an overlap are received.

9. The computer implemented method according to claim 1, wherein signals, at an assumed cyclic pressure change, are received at predetermined time intervals in a pressure change cycle.

10. The computer implemented method according to claim 1, wherein the signals come from a blood vessel wall and the data are received only during a specific time interval of the period of the heartbeat.

11. The computer implemented method according to claim 1, wherein the tissue is an artery moving during the heartbeat in the longitudinal direction, and the sensor is moved parallel to the longitudinal direction, so that, during at least one detection period, the sensor has a fixed position relative to the wall of the artery.

12. The method of claim 1 wherein the sufficient correlation is provided by determining an optimum overlap between image frames by use of a probability function representing similarity between consecutive signals.

13. An apparatus for generating hardness information of tissue subject to a varying pressure, wherein the apparatus comprises:
  a sensor adapted to record signals from tissue while being moved through a blood vessel or body cavity, wherein the apparatus is adapted to control the sensor to acquire signals from the tissue, during a period of varying pressure exerted on the tissue, while being controllably moved in a direction transverse to a measuring plane defined by the sensor;
  a processor device adapted to collect and process signals from the sensor to identify strain of the tissue and to relate the strain to elasticity and/or hardness parameters of a tissue surface or tissue volume part; and
  a display device for displaying elasticity and/or hardness parameters of the tissue surface or tissue volume part; and
  wherein the processor device is adapted to:
    receive the signals from the sensor for measuring the deformation of the tissue in a measuring plane defined by the sensor, and where the apparatus is further adapted to move the sensor, while the sensor is receiving signals from the tissue, under control of an actuator:
      (a) in a direction transverse to the measuring plane, and
      (b) while the tissue is subject to a varying pressure,
    identify strain of the tissue from the signals received by the sensor moved during the receiving signals step in the direction transverse to the measuring plane, and
    relate the strain to at least one of either hardness or elasticity parameters of the tissue; and
  wherein the apparatus is further adapted to control moving the sensor under control of the actuator, in the direction transverse to the measuring plane while the tissue is subject to a varying pressure, to provide sufficient correlation between consecutive image frames generated from the signals received by the sensor to identify strain of the tissue.

14. The apparatus of claim 13, wherein the apparatus comprises:
  a correlation detector for detecting correlation between consecutively acquired signals, where the signals are representative of the deformation of the tissue at positions of the sensor moved with respect to other positions of the sensor;
  the processor device being arranged to calculate by use of said correlation a strain in a tissue surface or tissue volume part extending parallel to the direction of motion of the sensor.

15. The apparatus of claim 13, wherein the apparatus further comprises:
  a position recorder coupled with the processor device to record sensor positions.

16. The apparatus of claim 13, wherein the apparatus further comprises:
  an actuator for controllably moving the sensor in the direction transverse to the measuring plane while the sensor acquires signals from the tissue.

17. The apparatus of claim 16, wherein the actuator has an adjustable speed Of motion.

18. The apparatus of claim 13, wherein the apparatus further comprises:
  an activator for activating non-transitory data storage for storing signals.

19. The apparatus of claim 13, wherein the apparatus comprises:
  an activator for activating the actuator.

20. The apparatus of claim 18, wherein the activator is adapted to be controlled by data from an ECG recording device to become active during a predetermined part of the heartbeat.

21. The apparatus of claim 18, wherein the activator is connected with the correlation detector to become active at a predetermined correlation.

22. The apparatus of claim 13, wherein the sensor is arranged in a catheter, adapted to be inserted into a blood vessel, the sensor being adapted to receive signals under controlled pullback of the catheter.

23. The apparatus of claim 13, wherein the sensor is an acoustic sensor.

24. The apparatus of claim 13, wherein the sensor is an optical sensor.

25. The apparatus of claim 13 wherein the apparatus is adapted to execute a probability function representing similarity between consecutive signals to provide the sufficient correlation by determining an optimum overlap between image frames.

* * * * *